(12) United States Patent
Bui et al.

(10) Patent No.: US 9,005,590 B2
(45) Date of Patent: *Apr. 14, 2015

(54) COMPOSITION COMPRISING A POLYOL, A SUGAR SILICONE SURFCTANT AND A OIL-SOLUBLE HIGH CARBON POLAR MODIFIED POLYMER

(75) Inventors: Hy Si Bui, Piscataway, NJ (US); Mohamed Kanji, Edison, NJ (US); Anita Chon Tong, Westfield, NJ (US); Susan Halpern, Paramus, NJ (US)

(73) Assignee: L'Oréal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/825,587

(22) Filed: Jun. 29, 2010

(65) Prior Publication Data

US 2010/0330015 A1    Dec. 30, 2010

Related U.S. Application Data

(60) Provisional application No. 61/221,341, filed on Jun. 29, 2009, provisional application No. 61/221,250, filed on Jun. 29, 2009.

(51) Int. Cl.

| | | |
|---|---|---|
| A61K 8/00 | (2006.01) |
| A61K 8/18 | (2006.01) |
| A61K 8/81 | (2006.01) |
| A61K 8/92 | (2006.01) |
| A61Q 1/04 | (2006.01) |
| A61Q 1/06 | (2006.01) |
| A61Q 1/10 | (2006.01) |
| A01N 31/00 | (2006.01) |
| A61K 8/31 | (2006.01) |
| A61K 8/891 | (2006.01) |
| A61K 8/898 | (2006.01) |
| A61Q 1/02 | (2006.01) |

(52) U.S. Cl.
CPC ... *A61Q 1/04* (2013.01); *A61K 8/31* (2013.01); *A61K 8/8164* (2013.01); *A61K 8/891* (2013.01); *A61K 8/898* (2013.01); *A61Q 1/02* (2013.01); *A61Q 1/06* (2013.01); *A61K 2800/544* (2013.01)

(58) Field of Classification Search
USPC .................................. 424/64, 70.7; 514/738
See application file for complete search history.

(56) References Cited

U.S. PATENT DOCUMENTS

| 8,551,461 | B2 | 10/2013 | Bui et al. |
|---|---|---|---|
| 8,597,621 | B2 | 12/2013 | Bui et al. |
| 2005/0180936 | A1* | 8/2005 | Pays ........................ 424/70.11 |
| 2006/0188459 | A1* | 8/2006 | Heinrichs et al. ............ 424/63 |
| 2007/0031361 | A1 | 2/2007 | Herrmann et al. |
| 2011/0020255 | A1 | 1/2011 | Bui et al. |
| 2011/0020259 | A1 | 1/2011 | Bui et al. |
| 2011/0223123 | A1 | 9/2011 | Bui et al. |
| 2011/0280817 | A1 | 11/2011 | Ramadan et al. |
| 2011/0280818 | A1 | 11/2011 | Kawaratani et al. |
| 2011/0280819 | A1 | 11/2011 | Bui et al. |
| 2011/0286949 | A1 | 11/2011 | Bui et al. |
| 2011/0286950 | A1 | 11/2011 | Bui et al. |
| 2011/0286951 | A1 | 11/2011 | Bui et al. |
| 2011/0286954 | A1 | 11/2011 | Bui et al. |
| 2011/0293550 | A1 | 12/2011 | Bui et al. |
| 2011/0311467 | A1 | 12/2011 | Bui et al. |
| 2012/0003169 | A1 | 1/2012 | Bui et al. |
| 2012/0004327 | A1 | 1/2012 | Bui et al. |
| 2012/0020907 | A1 | 1/2012 | Bui et al. |
| 2012/0171140 | A1 | 7/2012 | Bui et al. |
| 2014/0004069 | A1 | 1/2014 | Bui et al. |
| 2014/0037565 | A1 | 2/2014 | Bue, et al. |

FOREIGN PATENT DOCUMENTS

| DE | 100 64 799 | | 6/2002 |
|---|---|---|---|
| WO | WO 01/17485 | * | 3/2001 |
| WO | WO 2006/127883 | | 11/2006 |
| WO | WO 2007/048672 | * | 5/2007 |
| WO | WO 2007/139812 | | 12/2007 |
| WO | WO 2008/046763 | * | 4/2008 |

OTHER PUBLICATIONS

Vertellus, ZeMac(R) E400 Copolymer Technical Data Sheet.*
Hauthal, Tenside Surf. Det. 2008, 45 (1), 30-42.*
European Search Report dated Mar. 10, 2011, in European Application No. 10167784.7.
European Office Action from European Patent Application No. 10167784.7 dated Mar. 21, 2011 (4 pages).
U.S. Appl. No. 12/825,707, filed Jun. 29, 2010, Bui, et al.
U.S. Appl. No. 12/825,767, filed Jun. 29, 2010, Bui, et al.
U.S. Appl. No. 12/825,807, filed Jun. 29, 2010, Bui, et al.
U.S. Appl. No. 12/825,840, filed Jun. 29, 2010, Bui, et al.
U.S. Appl. No. 12/825,623, filed Jun. 29, 2010, Bui, et al.
U.S. Appl. No. 12/825,726, filed Jun. 29, 2010, Bui, et al.
U.S. Appl. No. 12/825,633, filed Jun. 29, 2010, Bui, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,730, filed Jun. 29, 2010, Bui, et al.
U.S. Appl. No. 12/825,614, filed Jun. 29, 2010, Bui, et al.
U.S. Appl. No. 12/825,600, filed Jun. 29, 2010, Bui, et al.
U.S. Appl. No. 12/825,559, filed Jun. 29, 2010, Bui, et al.
U.S. Appl. No. 13/133,176, filed Jun. 7, 2011, Bui, et al.
U.S. Appl. No. 13/133,181, filed Aug. 1, 2011, Bui, et al.
U.S. Appl. No. 13/379,691, filed Dec. 21, 2011, Bui, et al.
U.S. Appl. No. 14/241,753, filed Feb. 27, 2014, Motornov, et al.
U.S. Appl. No. 14/227,264, filed Mar. 27, 2014, Bui, et al.
U.S. Appl. No. 14/147,726, filed Jan. 6, 2014, Bui, et al.
U.S. Appl. No. 14/241,361, filed Feb. 26, 2014, Motornov, et al.

* cited by examiner

*Primary Examiner* — Gina Justice
*Assistant Examiner* — Genevieve S Alley
(74) *Attorney, Agent, or Firm* — Oblon, McClelland, Maier & Neustadt, L.L.P.

(57) ABSTRACT

The invention relates to a composition comprising a oil-soluble high carbon polar modified polymer, a sugar silicone surfactant and a hyperbranched polyol.

14 Claims, No Drawings

COMPOSITION COMPRISING A POLYOL, A SUGAR SILICONE SURFCTANT AND A OIL-SOLUBLE HIGH CARBON POLAR MODIFIED POLYMER

CROSS-REFERENCE TO RELATED APPLICATIONS

This application claims the benefit of priority from U.S. Provisional Application Ser. Nos. 61/221,341 and 61/221,250, both filed Jun. 29, 2009, the entire contents of which are hereby incorporated by reference.

FIELD OF THE INVENTION

The present invention relates to a composition comprising at least one hyperbranched polyol having at least two hydroxyl groups, a sugar silicone surfactant and at least one oil-soluble high carbon polar modified polymer. Such compositions have industrial, pharmacological and/or cosmetic applicability.

DISCUSSION OF THE BACKGROUND

U.S. Pat. No. 6,492,455 discloses water-soluble reaction products of polyamines and C6 olefin/maleic anhydride copolymers. Because these compositions are water-soluble, addition of water to such reaction products renders the products unsuitable for applications requiring water-insolubility. For example, such reaction products are unsuitable for use as a solid carrier containing colorant (for example, industrial pigments) or active agents (for example, pharmaceuticals) because the reaction product breaks down upon exposure to water.

Thus, there remains a need for improved products which can function as a carrier and/or matrix for desired agents.

Further, a problem with conventional lip make up products is their inability to continuously hydrate and moisturize the lips. The reason for this is that water either has to be deposited onto the lips from the gloss itself or drawn to the lips from the atmosphere. In the event that the source of water for hydration is the product itself, it is very difficult to maintain the water in a stabilized form. Failure to do so results in the water quickly evaporating from the surface of the lips leaving the lips feeling dry.

Also, conventional lip compositions which impart a high degree of gloss onto the lip surface require the presence of silicone fluids in the composition. Silicone fluids are known to have high refractive indices which provide shine. These types of silicone fluids, however, have poor environmental profiles and are relatively expensive.

Therefore, it is desirable to provide lip compositions, having a high degree of gloss, which are capable of hydrating and/or moisturizing the lips in a continuous manner.

SUMMARY OF THE INVENTION

The present invention relates to a composition comprising at least one polyol having at least two hydroxyl groups, at least one sugar silicone surfactant and at least one oil-soluble high carbon polar modified polymer.

The present invention also relates to compositions comprising at least one polyol having at least two hydroxyl groups, at least one sugar silicone surfactant, at least one oil-soluble high carbon polar modified polymer, and a desired agent such as a colorant or pharmacologically active agent.

The present invention also relates to compositions, preferably solid compositions, comprising at least one polyol having at least two hydroxyl groups, at least one sugar silicone surfactant, at least one oil-soluble high carbon polar modified polymer, and water. Preferably, such compositions further comprise a desired agent.

The present invention also relates to compositions, preferably solid compositions, comprising at least one polyol having at least two hydroxyl groups, at least one sugar silicone surfactant, at least one oil-soluble high carbon polar modified polymer, and at least one oil. Preferably, such compositions further comprise a desired agent.

The present invention also relates to methods of treating, caring for and/or making up keratinous material (for example, skin, eyes, eyelashes or lips) by applying cosmetic compositions of the present invention to the keratinous material in an amount sufficient to treat, care for and/or make up the keratinous material.

The present invention also relates to methods of improving the feel or texture properties of a cosmetic composition upon application to a keratin material, comprising forming a composition comprising at least one polyol having at least two hydroxyl groups, at least one sugar silicone surfactant and at least one oil-soluble high carbon polar modified polymer.

The present invention also relates to methods of applying the above-disclosed compositions onto the lips in an amount sufficient to make up, provide color, and/or provide hydration or moisturization to the lips. It has been surprisingly found that compositions, according to an embodiment of the present invention impart glossy, non-sticky hydration and moisturization to the lips.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100□ C.

"Non-volatile", as used herein, means having a flash point of greater than about 100□ C.

The compositions and methods of the present invention can comprise, consist of, or consist essentially of the essential elements and limitations of the invention described herein, as well as any additional or optional ingredients, components, or limitations described herein or otherwise useful.

In accordance with the present invention, the "hardness" of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf, including all ranges and subranges therebetween.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is □50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

Oil-Soluble High Carbon Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinilty of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil-soluble high carbon polar modified polymer(s) represent from about 1% to about 20% of the total weight of the composition, more preferably from about 3% to about 17% of the total weight of the composition, and most preferably from about 5% to about 15%, including all ranges and subranges therebetween.

Hyperbranched Polyol Compound

According to the present invention, compositions comprising at least one hyperbranched polyol compound are provided. In accordance with the present invention, the hyperbranched polyol compound has at least two hydroxyl groups available to react with hydrophilic groups on the backbone of the polar modified wax.

"Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample. According to preferred embodiments, the at least one hyperbranched polyol has a hydroxyl number between 50 and 250, preferably between 75 and 225, preferably between 100 and 200, preferably between 125 and 175, including all ranges and subranges therebetween such as 90 to 150.

In accordance with the present invention, "hyperbranched polyol" refers to dendrimers, hyperbranched macromolecules and other dendron-based architectures. Hyperbranched polyols can generally be described as three-dimensional highly branched molecules having a tree-like structure.

They are characterized by a great number of end groups, at least two of which are hydroxyl groups. The dendritic or "tree-like" structure preferably shows regular symmetric branching from a central multifunctional core molecule leading to a compact globular or quasi-globular structure with a large number of end groups per molecule. Suitable examples of hyperbranched polyols can be found in U.S. Pat. No. 7,423,104, and U.S. patent applications 2008/0207871 and 2008/0286152, the entire contents of all of which are hereby incorporated by reference. Other suitable examples include alcohol functional olefinic polymers such as those available from New Phase Technologies.

Dendrimers tend to be exact, monodisperse structures built layerwise (in generations) around a core moiety, with a polymer branching point in every repeating unit. Hyperbranched polymers tend to possess a number of characteristics which are similar to dendrimers but they tend to be polydispersed and contain relatively linear segments off of which a plurality of highly branched segments are grown or attached.

Furthermore, "hyperbranched polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

According to particularly preferred embodiments of the present invention, the hyperbranched polyol comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are acyclic, cyclic, polycyclic, terminal a, internal, linear, branched, substituted, unsubstituted, functionalized, and/or non-functionalized. For example, suitable monomers include ethylene, propylene, 1-butene, 2-butene, 3-methyl-1-butene, and isobutylene.

Suitable silicone groups for inclusion into the interior chain include "D" groups (for example, dimethicone or substituted dimethicone groups).

An exemplary structure is as follows:

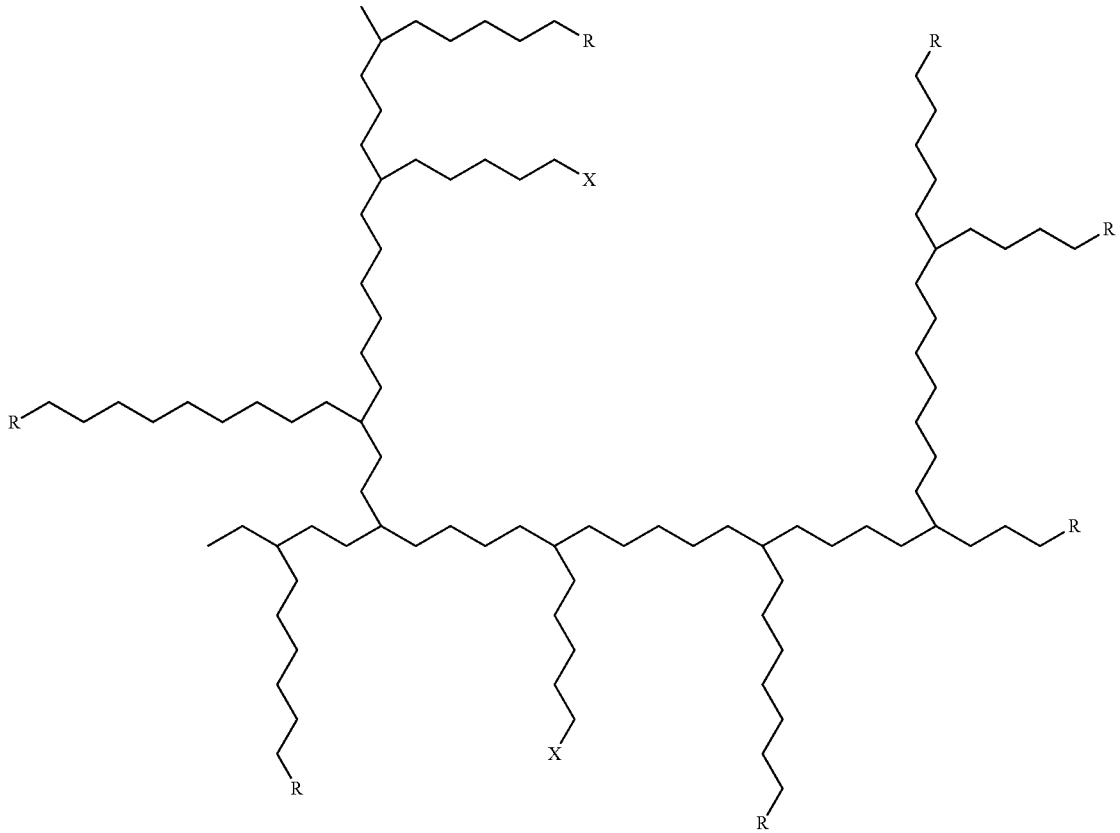

Where X corresponds to hydroxyl functionality and R corresponds to a methyl group or an alkyl group preferably containing 2-30 atoms.

According to preferred embodiments, the at least one hyperbranched polyol has a molecular weight (Mw) between about 3,000 and 25,000, preferably between 4,000 and 22,000, preferably between 5,000 and 20,000, including all ranges and subranges therebetween such as 4000 to 5500.

According to preferred embodiments, the at least one hyperbranched polyol has a viscosity at 90° F. of between 1,000 and 8,000 centipoise (cps), preferably 2,000 and 7,000 cps, and preferably 3,000 and 6,000 cps, including all ranges and subranges therebetween.

According to preferred embodiments, the at least one hyperbranched polyol is present in the composition of the present invention in an amount ranging from about 0.1 to about 15% by weight, more preferably from about 1 to about 10% by weight, most preferably from about 2 to about 8% by weight, based on the total weight of the composition, including all ranges and subranges within these ranges.

Preferably, the weight ratio of polyol to oil-soluble high carbon polar modified polymer is between 4:1 and 1:4, preferably between 3:1 and 1:3, and preferably between 2:1 and 1:2, including all ranges and subranges therebetween.

According to preferred embodiments, the oil-soluble high carbon polar modified polymer is in an oil carrier, and the polyol is blended into the oil carrier during production of the compositions of the present invention. Because the oil-soluble high carbon polar modified polymer is typically solid at room temperature, the oil carrier is preferably heated to liquefy the wax prior to combination with the polyol. Preferably, the oil carrier is heated beyond the melting point of the Oil-soluble polar modified polymer, typically up to about 70° C., 80° C., 90° C., 100° C. or 110° C. Then, the polar modified wax is preferably combined with the polyol through blending at room temperature or at a slightly elevated temperature (that is, at a temperature between room temperature and the temperature at which the polar modified wax was liquefied or melted) such as, for example, about 30° C., 40° C., 50° C., 60° C. or 70° C., for at least about 30 minutes.

According to some embodiments of the present invention, the polyol can be in an aqueous carrier, and the polar modified wax can be combined with the polyol by combining the oil carrier with the aqueous carrier. According to other embodiments, the polyol does not have to be in an aqueous carrier—the polyol can be added to the oil carrier first, and then water can be subsequently added to the mixture.

According to preferred embodiments, the oil carrier comprises volatile and/or non-volatile oils. Such oils can be any acceptable oil including but not limited to silicone oils and/or hydrocarbon oils.

According to preferred embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

The volatility of the solvents/oils can be determined using the evaporation speed as set forth in U.S. Pat. No. 6,338,839, the contents of which are incorporated by reference herein.

According to preferred embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6+R7☐10, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

C8 to C26 fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Sugar Silicone Surfactant

According to the present invention, compositions comprising at least one sugar silicone surfactant are provided. The sugar silicone surfactant of the present invention has the following formula:

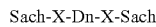

Sach-X-Dn-X-Sach where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosylsucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula R2SiO, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, lactobionolactonesiloxane, or a mixture thereof.

Preferably, the sugar silicone surfactant represents from about 0.5% to about 25% of the total weight of the composition, more preferably from about 0.75% to about 15% of the total weight of the composition, and most preferably from about 1% to about 10%, including all ranges and subranges therebetween.

According to preferred embodiments of the present invention, a desired agent can be incorporated within the composition. The desired agent can be, for example, any colorant (pigment, dye, etc.), any pharmaceutically or cosmetically active agent, or any film forming agent known in the art. Such a desired agent can be incorporated into the composition of the present invention and can be active during subsequent use of the composition. For example, a cosmetic makeup composition or a paint composition comprising colorant can provide colorant and/or film forming agent to a substrate (skin, lips, wall, frame, etc.) during use to provide the substrate with the desired film and/or color. Similarly, a pharmaceutical or cosmetic composition comprising a pharmaceutically active agent can provide such active agent to the patient or consumer upon use (for example, a transdermal patch within which is a pharmaceutically or cosmetically active agent, or a tablet or capsule containing the active agent).

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a C2 to C30, such as C3 to C22 alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, polyethylene oxide) based thickeners, sodium carbomer, and mixtures thereof.

According to preferred embodiments of the present invention, compositions of the present invention can comprise substantial amounts of water. Preferably, compositions of the present invention comprise from about 5% to about 50% water, more preferably from about 15% to about 45% water, and more preferably from about 25% to about 40% water by weight with respect to the total weight of the composition, including all ranges and subranges therebetween. According to particularly preferred embodiments, compositions of the present invention and at least 25% water are solid compositions. Such solid compositions are preferably in the form of a stick (for example, a lipstick or a stick foundation).

Compositions of the present invention can optionally further comprise any additive usually used in the field(s) under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which are hereby incorporated by reference. Further examples of suitable additional components can be found in the other references which have been incorporated by reference in this application. Still further examples of such additional ingredients may be found in the International Cosmetic Ingredient Dictionary and Handbook (9th ed. 2002).

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

Another particularly preferred embodiment of the present invention is a composition which contains so little elastomer that the presence of such elastomer not affect the cosmetic properties of the composition. Preferably, the compositions are substantially free of such elastomers (i.e., contain less than about 0.5% elastomer), essentially free of such elastomers (i.e., contain less than about 0.25% elastomer) or free of such elastomer (i.e., contain no elastomer).

According to other embodiments of the present invention, the compositions of the present invention are anhydrous. By "anhydrous," it is meant that the composition contains substantially no water (that is, less than about 5% by weight of the composition of water).

According to other preferred embodiments, methods of treating, caring for and/or enhancing the appearance of keratinous material by applying compositions of the present invention to the keratinous material in an amount sufficient to treat, care for and/or enhance the appearance of the keratinous material are provided. In accordance with these preceding preferred embodiments, the compositions of the present invention comprising at least one polar modified wax, at least one sugar silicone surfactant and at least one polyol compound are applied topically to the desired area of the keratin material in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved waterproof characteristics, improved feel upon application (for example, texture, reduced drag or tackiness), and/or increased shine/color characteristics are provided.

According to other embodiments of the present invention, methods of improving the texture and/or shine/color properties of a composition, comprising adding at least one oil-soluble high carbon polar modified polymer, at least one sugar silicone surfactant and at least one polyol to the composition are provided. In accordance with this embodiment, the at least one oil-soluble high carbon polar modified polymer, the at least one sugar silicone surfactant and the at least one polyol are present in amounts sufficient to achieve the desired result.

According to other embodiments of the present invention, methods of moisturizing or hydrating keratinous material such as lips or skin by applying the compositions of the present invention to the keratinous material are provided. It has surprisingly been discovered that the association of a sugar silicone surfactant with the above-described polar modified polymer results in the formation of a stable emulsion capable of imparting high gloss onto the lips, in the absence of any conventional silicone fluids used to provide shine. Moreover, the use of the sugar silicone surfactant eliminates the need for using surfactant/emulsifiers to form the stable emulsion. Finally, the resultant composition, when applied onto the lips, both hydrates and moisturizes the lips dues to the large amount of water entrapped therein, while at the same time making the lips feel unusually refreshed and pleasant.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

Lipstick Composition

| Phase | Chemical Name | Example 1 |
| --- | --- | --- |
| A | Non-volatile Solvent | Q.S. |
| A | Hyperbranched polyol | 5.00 |
| A | Polyethylene 400 | 8.00 |
| A | C26-28 Polar Modified Wax | 7.00 |
| A | Pigment | 3.50 |
| A | Mica | 2.00 |
| B | Deionized Water | 22.50 |
| B | Glycerin | 3.00 |
| B | Sugar Silicone Surfactant | 10.00 |
| | Total | 100.00 |

Procedure:

The following were added to a suitable size beaker A and heated to 95 Celsius degrees: non-volatile solvent, hyperbranched polyol, polyethylene 400, C26-28 Polar Modified Wax.

When enough solids had melted, the contents were mixed with moderate speed until all solids had melted at 95 Celsius degrees.

The temperature was slightly lowered to 85 Celsius degrees and pigments and mica were added.

The contents of main beaker A was transferred to a Silverson mixer for emulsification while maintaining the temperature at 85-90 Celsius degrees.

In a separate beaker 2, glycerin, and sugar silicone surfactant were added into DI water and mixed and heated to 85 Celsius degrees.

The contents of side beaker B was added dropwise into the beaker A while emulsifying at 9000 rpm under the Silverson mixer for 30 minutes. Afterward, the emulsification speed was lowered to 2000 rpm for 5 minutes.

The contents were poured into lipstick molds at 80 Celsius degrees.

The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

Example 2

Lip Gloss

| Phase | Chemical Name | Example 2 |
|---|---|---|
| A | Non-volatile Solvent | Q.S. |
| A | C26-28 Polar Modified Wax | 7.00 |
| A | Hyperbranched polyol | 5.00 |
| A | Pigment | 3.50 |
| A | Mica | 2.00 |
| B | Deionized Water | 40.00 |
| B | Glycerin | 3.00 |
| B | Sugar Silicone Surfactant | 10.00 |
| | Total | 100.00 |

Procedure:

The following were added to a suitable size beaker A and heated to 95 Celsius degrees: non-volatile solvent, hyperbranched polyol, C26-28 Polar Modified Wax.

When enough solids had melted, the contents were mixed with moderate speed until all solids had melted at 95 Celsius degrees.

The temperature was slightly lowered to 85 Celsius degrees and pigments and mica were added.

The contents of main beaker A was transferred to a Silverson mixer for emulsification while maintaining the temperature at 85-90 Celsius degrees.

In a separate beaker 2, glycerin, and sugar silicone surfactant were added into DI water and mixed and heated to 85 Celsius degrees.

The contents of side beaker B was added dropwise into the beaker A while emulsifying at 9000 rpm under the Silverson mixer for 30 minutes. Afterward, the emulsification speed was lowered to 2000 rpm for 5 minutes until contents were cooled to 25 Celsius degrees.

The contents of main beaker A was poured into container.

Example 3

Foundation Composition

| | Chemical Name | Weight % |
|---|---|---|
| A | isododecane | 31.6 |
| | isohexadecane | 2.25 |
| | C26-28 Polar Modified Wax | 10 |
| | polyglyceryl-2 triisostearate | 2.5 |
| | hyperbranched polyol | 5 |
| | TITANIUM DIOXIDE | 7.82 |
| | IRON OXIDES | 2.18 |
| B | DI Water | 22 |
| | cellulose | 0.15 |
| | sugar silicone surfactant | 15 |
| | DISODIUM EDTA | 0.20 |
| | propylene glycol | 0.50 |
| | PHENOXY-2 ETHANOL | 0.40 |

-continued

| Chemical Name | Weight % |
|---|---|
| CHLORPHENESIN | 0.20 |
| ETHYL PARABEN | 0.2 |
| | 100 |

Procedure

In container A, C26-28 Polar Modified Wax and hyperbranched polyol were melted in the isohexadecane and isododecane until fully dissolved. The temperature was brought to 900 C.

While maintaining the temperature, polyglyceryl-2 triisostearate, titanium dioxide, and iron oxides were added to container A until fully dissolved.

In a separate container B, water, cellulose, sugar silicone surfactant, disodium EDTA, propylene glycol and preservatives were mixed and heated to 900 C.

The contents of container B were added to the contents of container A slowly at high sheer (~1000 rpm).

Heat was maintained at 700 C-800 C for 20 minutes while maintaining high sheer mixing.

The mixture was cooled to room temperature while mixing.

What is claimed is:

1. A composition comprising:
   (a) water;
   (b) at least one oil-soluble high carbon polar modified polymer consisting of C26-C28 monomers, and maleic anhydride units, and wherein said polymer has a weight-average molecular weight of less than or equal to 30000 g/mol and a crystallinity of 8% to 60%;
   (c) a surfactant system comprising at least one sugar silicone surfactant; and
   (d) at least one hyperbranched polyol having at least two hydroxyl groups,
   wherein the composition is in the form of an emulsion.

2. The composition of claim 1, further comprising at least one colorant.

3. The composition of claim 1, wherein the composition comprises water in an amount ranging from about 25% to about 50% by weight with respect to the weight of the composition.

4. The composition of claim 1, wherein the composition is solid.

5. The composition of claim 1, wherein the composition is a mascara, a lipstick or a foundation.

6. The composition of claim 1, wherein the oil-soluble high carbon polar modified polymer is present in an amount of from about 1% to about 20% by weight, based on the weight of the composition.

7. The composition of claim 1, wherein the oil-soluble high carbon polar modified polymer is present in an amount of from about 1% to about 20% by weight, based on the weight of the composition.

8. The composition of claim 1, wherein the sugar silicone surfactant is gluconamidoethylaminopropylsilicone.

9. The composition of claim 1, wherein the sugar silicone surfactant is present in an amount of from about 0.05 to about 25% by weight, based on the weight of the composition.

10. The composition of claim 1, wherein the hyperbranched polyol is present in an amount ranging from about 0.1 to about 15% by weight based on the total weight of the composition.

11. The composition of claim 1, wherein the weight-average molecular weight of the oil-soluble high carbon polar modified polymer is from 500 to 10,000 g/mol.

12. The composition of claim 1, wherein the oil-soluble high carbon polar modified polymer has from about 5% to about 30% maleic anhydride units by weight with respect to the weight of the oil soluble high carbon polar modified polymer.

13. The composition of claim 1, wherein the oil-soluble high carbon polar modified polymer has from about 10% to about 25% maleic anhydride units by weight with respect to the weight of the oil soluble high carbon polar modified polymer.

14. The composition of claim 1, wherein the surfactant system consists essentially of the at least one silicone sugar surfactant.

* * * * *